United States Patent
Patry et al.

(10) Patent No.: US 10,538,617 B2
(45) Date of Patent: Jan. 21, 2020

(54) FATTY ACID POLYESTER DERIVATIVES OF POLYGLYCOSIDES

(71) Applicants: UNIVERSITE DE MONTPELLIER, Montpellier (FR); CENTRE NATIONAL DE LA RECHERCHE SCIENTIFIQUE, Paris (FR)

(72) Inventors: Stéphane Patry, Voiron (FR); Jean-Pierre Habas, Montpellier (FR)

(73) Assignees: UNIVERSITE DE MONTPELLIER, Montpellier (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/504,872

(22) PCT Filed: Jul. 21, 2015

(86) PCT No.: PCT/EP2015/066690
§ 371 (c)(1),
(2) Date: Feb. 17, 2017

(87) PCT Pub. No.: WO2016/026641
PCT Pub. Date: Feb. 25, 2016

(65) Prior Publication Data
US 2017/0275415 A1    Sep. 28, 2017

(30) Foreign Application Priority Data
Aug. 22, 2014 (FR) ...................................... 14 57946

(51) Int. Cl.
*C07H 15/203* (2006.01)
*C07H 13/06* (2006.01)
(Continued)

(52) U.S. Cl.
CPC ......... *C08G 59/3236* (2013.01); *C07H 13/06* (2013.01); *C07H 15/203* (2013.01); *C08G 59/4238* (2013.01); *C08G 59/5026* (2013.01)

(58) Field of Classification Search
None
See application file for complete search history.

(56) References Cited

U.S. PATENT DOCUMENTS

| 4,517,360 A | 5/1985 | Volpenhein |
| 4,973,489 A | 11/1990 | Meyer et al. |

(Continued)

FOREIGN PATENT DOCUMENTS

| DE | 156263 | 8/1982 | |
| EP | 0132941 A1 * | 2/1985 | ............ C07H 13/06 |
| WO | WO-2011097484 A1 * | 8/2011 | ........... C08G 59/027 |

OTHER PUBLICATIONS

Smits et al. titled Reliable method for the synthesis of aryl B-D-glyopyranosides using BTF-diethyl ether as a catalyst. (Year: 1996).*
(Continued)

*Primary Examiner* — Peter A Salamon
(74) *Attorney, Agent, or Firm* — Greer, Burns & Crain, Ltd.

(57) ABSTRACT

Fatty acid polyester derivatives of polyglycosides formed from a polyol having between 2 and 10 hydroxy functions, the 2 hydroxy functions or at least 2 of these hydroxy functions being bound to the anomeric carbon of a reducing carbohydrate that is identical or different for each hydroxy group and selected from the monosaccharides and disaccharides, in which at least one of the other hydroxy groups of the monosaccharide or the disaccharide is esterified by a lipid derivative bearing at least one double bond optionally originating from a vegetable or animal oil, from a mixture of vegetable or animal oils, the double bond or the at least one of the double bonds of the lipid derivative being function- (Continued)

alized by a group selected from the epoxy, amine, alcohol and acid groups, and use thereof in particular in reaction formulations for the production of polymer materials.

12 Claims, 5 Drawing Sheets

(51) Int. Cl.
*C08G 59/32* (2006.01)
*C08G 59/42* (2006.01)
*C08G 59/50* (2006.01)

(56) References Cited

U.S. PATENT DOCUMENTS

| | | | |
|---|---|---|---|
| 6,121,440 | A | 9/2000 | Kenneally et al. |
| 6,995,232 | B2 | 2/2006 | Howie et al. |
| 7,622,563 | B2 | 11/2009 | Furuya et al. |
| 9,096,773 | B2 * | 8/2015 | Webster ............... C08G 59/027 |
| 9,108,908 | B2 | 8/2015 | Caillol et al. |
| 2006/0020062 | A1 * | 1/2006 | Bloom ................ C07D 303/42 524/114 |
| 2014/0083636 | A1 | 3/2014 | Habas et al. |
| 2014/0336301 | A1 * | 11/2014 | Webster ............... C08G 59/027 522/170 |
| 2015/0011680 | A1 | 1/2015 | Habas et al. |
| 2017/0275415 | A1 * | 9/2017 | Patry .................... C07H 15/203 |

OTHER PUBLICATIONS

Akoh et al. "One-Stage Synthesis of Raffinose Fatty Acid Polyesters" Journal of Food Science (1987), 52(6), pp. 1570-1576.

Akoh et al. "Optimized Synthesis of Sucrose Polyesters: Comparison of Physical Properties of Sucrose Polyesters, Raffinose Polyesters and Salad Oils" Journal of Food Science (1990), 55(1), pp. 236-243.

Akoh et al. "Preparation of Trehalose and Sorbitol Fatty Acid Polyesters by Interesterification" Journal of the American Oil Chemists' Society (1989), 66(11), pp. 1581-1587.

Bergeron-Brlek et al. "Palladium-Catalyzed Ullman-Type Reductive Homocoupling of Iodoaryl Glycosides" Journal of Organic Chemistry (2012), 77(6), pp. 2971-2977.

Corma et al. "Chemical Routes for the Transformation of Biomass into Chemicals" Chemical Reviews (2007), 107(6), pp. 2411-2502.

Desroches et al. "From Vegetable Oils to Polyurethanes: Synthetic Routes to Polyols and Main Industrial Products" Polymer Reviews (2012), 52(1), pp. 38-79.

Dondoni et al. "Synthesis of All Carbon Linked Glycoside Clusters Round Benzene Scaffold via Sonogashira-Heck-Cassar Cross-Coupling of Iodobenzenes with Ethynyl C-Glycosides" Synlett (2002), No. 11, pp. 1850-1854.

Giguère et al. "Synthesis of Stable and Selective Inhibitors of Human Galectins-1 and -3" Bioorganic & Medicinal Chemistry (2008), 16(16), pp. 7811-7823.

Güner et al. "Polymers from Triglyceride Oils" Progress in Polymer Science (2006), 31(7), pp. 633-670.

Kandanarachchi et al. "The Hydroformylation of Vegetable Oils and Model Compounds by Ligand Modified Rhodium Catalysis" Journal of Molecular Catalysis (2002), 184(1-2), pp. 65-71.

Marra et al. "Validation of the Copper(I)-Catalyzed Azide-Alkyne Coupling in Ionic Liquids. Synthesis of a Triazole-Linked C-Disaccharide as a Case Study" Journal of Organic Chemistry (2008), 73(6), pp. 2458-2461.

Neto et al. "Novel Class of Non-Ionic Monocatenary and Bolaform Alkylglycoside Surfactants. Synthesis by Microwave-Assisted Glycosylation and Olefin Cross-Metathesis or by 'Click-Chemistry': Physicochemical Studies" Tetrahedron (2010), 66(25), pp. 4633-4646.

Pan et al. "Novel Biobased Epoxy Compounds: Epoxidized Sucrose Esters of Fatty Acids" Green Chemistry (2011), 13(4), pp. 965-975.

Pan et al. "High Biobased Content Epoxy-Anhydride Thermosets from Epoxidized Sucrose Esters of Fatty Acids" Biomacromolecules (2011), 12(6), pp. 2416-2428.

Roy et al. "Recent Applications of Olefin Metathesis and Related Reactions in Carbohydrate Chemistry" Chemical communications (2000), No. 7, pp. 519-529.

Siemsen et al. "Acetylenic Coupling: A Powerful Tool in Molecular Construction" Angewandte Chemie International Edition (2000), 39(15), pp. 2632-2657.

Smits et al. "Reliable Method for the Synthesis of Aryl β-D-Glucopyranosides, Using Boron Trifluoride-Diethyl Ether as Catalyst" Journal of the Chemical Society: Perkin Transactions 1 (1996), No. 24, pp. 2873-2877.

Stefanoiu et al. "Kinetics and Mechanism of the Reaction Between Maleic Anhydride and Fatty Acid Esters and the Structure of the Products" European Journal of Lipid Science and Technology (2008), 110(5), pp. 441-447.

Stemmelen et al. "A Fully Biobased Epoxy Resin from Vegetable Oils: From the Synthesis of the Precursors by Thiol-ene Reaction to the Study of the Final Material" Journal of Polymer Science Part A: Polymer Chemistry (2011), 49(11), pp. 2434-2444.

French Search Report from French Patent Application No. 1457946, dated Apr. 24, 2015.

International Search Report from International Patent Application No. PCT/EP2015/066690, dated Oct. 12, 2015.

\* cited by examiner

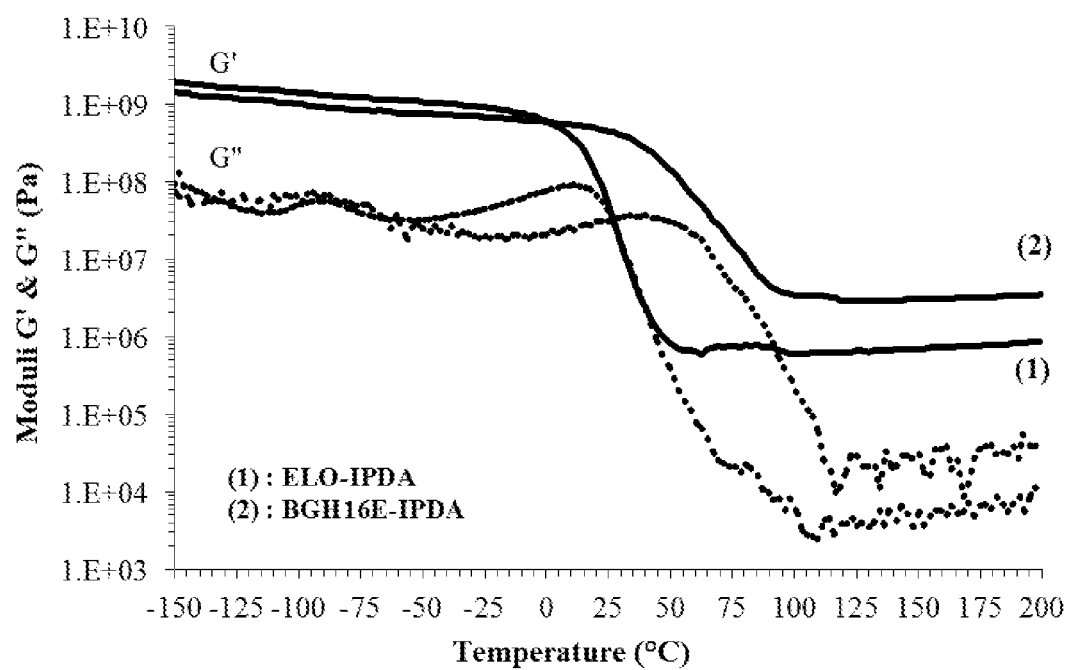

FATTY ACID POLYESTER DERIVATIVES OF POLYGLYCOSIDES

BACKGROUND

The present invention relates to biosourced fatty acid polyester derivatives of polyglycosides, the preparation process and use thereof as synthons in the preparation of different materials.

Synthetic polymers form part of daily life. Light, strong, insulating, easy to use, they are utilized in sectors as diverse as construction, packaging, the electrical and electronics industry, electrical goods, the toy sector and transport (automobile, railway, aeronautical, etc.). The limited and fossil nature of petroleum resources and considerations relating to the quality of the environment (global warming, waste management) provide a genuine opportunity for biosourced polymers, namely no longer originating from petroleum but from biomass.

Among these polymers, the epoxy resins, through their physico-chemical properties (mechanical, electrical, etc.) constitute a versatile class of thermosetting polymers that are very widely used in the fields of electronics, construction, paints or also transport. The vast majority of those currently on the market are of petrochemical origin. They are formed by mixing one (or more) "epoxy prepolymer(s)" (in other words a molecule bearing epoxy reactive groups) with a hardener also denoted by the term "cross-linking agent". These two families of components (prepolymer and hardener) react together by polymerization which, depending on the functionality of the chemical species involved, can generate the production of a three-dimensional polymer network. The epoxy resins are then referred to as cross-linked.

Many epoxy formulations make use of a prepolymer sourced from oil, bisphenol A diglycidyl ether (or BADGE). Now the latter is formulated from bisphenol A which is a compound classified as CMR (carcinogenic mutagenic reprotoxic). Its epoxidation is itself open to criticism on health grounds as it makes use of epichlorohydrin, the chemical toxicity of which is currently a subject of debate and the use of which is itself likely to be restricted or even discontinued in the medium term.

Thus, in order to find a response to increasingly stringent regulatory restrictions (REACH, RoHS, etc.) as well as facing up to the inevitable exhaustion of petroleum resources, diverse research has been carried out in order to try to develop materials, notably polymers, in particular epoxy resins, originating from biomass.

Thus the inventors have described, in application WO 2013/124574, epoxy resins comprising the product of the reaction of one or more biosourced epoxidized lipid derivatives extracted from a natural vegetable oil, with at least one cross-linking agent, in the presence of at least one co-reagent selected from the glycidyl ether derivatives of biosourced polyols.

The inventors have subsequently sought, on the one hand to further enhance the performances of these biosourced resins, in particular in terms of the glass transition temperature, and on the other hand to develop a versatile approach allowing the creation of platform molecules with chemical characteristics (nature and number of functionalities) allowing a wide range of forms ((polyepoxy, polyamine, polyols etc.) and therefore of potential applications.

French patent FR2962131 describes fatty substances of natural origin functionalized with primary alcohol functions or primary amine functions by a reaction of the thiol-ene type and use thereof in order to prepare, by polycondensation, polymers of different types: polyamides, polyurethanes, epoxy resins.

U.S. Pat. No. 6,995,232 describes the synthesis of sucrose polyesters (SEFOSE) by the reaction of individual fatty acid esters with sucrose. The final structure is thus formed by a saccharide-type core (a glucose ring "naturally" linked to a fructose ring) onto which up to eight fatty chains (SEFOSE) are grafted.

International application WO 2011/097484 describes the functionalization by epoxidation of the SEFOSEs described by U.S. Pat. No. 6,995,232 and international application WO02/060975. Strictly speaking, the chemical concept proposed relates only to the so-called epoxidation phase and allows no modulation of the central core of the initial molecular structures that is however essential to versatility of function and use.

However, there is still a need to have versatile molecular structures available, in order to allow the manufacture of materials that are partially or completely biosourced and having a wide range of mechanical characteristics, in particular in order to compete with those of the polymers of petrochemical origin and in order to adapt to numerous functions of final use.

SUMMARY

Now the Inventors have discovered that by grafting individual fatty chains (in particular fatty acids originating from vegetable oils or fatty acid esters originating from vegetable oils) onto a biosourced structure which can be modulated as it is based on reducing sugars bound to each other by a segment of an aliphatic, cycloaliphatic or aromatic nature making it possible to modulate the rigidity of the central core, it was possible to obtain a wide range of molecules by adjusting either the nature of the central core, or the functionalization of the grafted fatty chains. Each has specific properties thus making it possible to fulfill precise functions and ultimately to satisfy a great versatility of potential applications.

Thus, a subject of the present invention is fatty acid polyester derivatives of polyglycosides formed from a polyol comprising between 2 and 10 hydroxy functions, advantageously between 2 and 5 hydroxy functions, the 2 hydroxy functions or at least 2 of these hydroxy functions being bound to the anomeric carbon of a reducing carbohydrate that is identical or different for each hydroxy group and selected from the monosaccharides and disaccharides, in which at least one of the other hydroxy groups of said monosaccharide or disaccharide is esterified by a lipid derivative bearing at least one double bond and optionally originating from a vegetable or animal oil or from a mixture of vegetable or animal oils, the double bond or the at least one of the double bonds of said lipid derivative being functionalized by a group selected from the epoxy, amine, alcohol and acid groups.

According to the invention the hydroxy functions of the mono- or disaccharide functions that are not esterified by unsaturated lipid chains (chains bearing at least one double bond) can be either free, or esterified by a saturated $C_4$-$C_{36}$, advantageously $C_{12}$-$C_{20}$ lipid chain.

Within the meaning of the present invention, the term "biosourced" denotes a product originating from biomass. Biomass describes the total mass of living organisms of vegetable or animal origin in a defined habitat, called biotope, and the resources resulting therefrom via direct, indirect or potential use for humanity.

In an advantageous embodiment of the invention, the fatty acid polyester derivatives of polyglycosides correspond to formula (I)

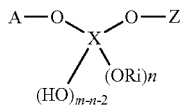

(I)

in which
- A and Z each represent, independently of each other, a reducing carbohydrate selected from the group of monosaccharides comprising glucose, fructose, galactose and mannose or from the group of the disaccharides comprising lactose and maltose,
  - said monosaccharides and said disaccharides being bound to —O—X—O— by their anomeric carbon initially bearing the hemiacetal OH,
  - at least one of the other OH groups of said monosaccharide or said disaccharide being esterified by a lipid derivative bearing at least one double bond optionally originating from a vegetable or animal oil or from a mixture of vegetable or animal oils,
  - the double bond or the at least one of the double bonds of said lipid derivative being functionalized by a group selected from the epoxy, amine, alcohol and acid groups,
- X represents a chemical structure bearing hydroxy functions in a compound selected from the group comprising the aliphatic (non-cyclic chains), cycloaliphatic and aromatic polyols,
- $R_i$ represents either a substituent, or several substituents denoted $R_a$ to $R_h$, said substituents $R_a$ to $R_h$, identical or different, being reducing carbohydrates selected from the group of monosaccharides comprising glucose, fructose, galactose and mannose or from the group of the disaccharides comprising lactose and maltose,
  - said monosaccharides and said disaccharides being bound to —O—X—O— by their anomeric carbon initially bearing the hemiacetal OH,
  - at least one of the other OH groups of said monosaccharide or said disaccharide being esterified by a lipid derivative bearing at least one double bond optionally originating from a vegetable or animal oil or from a mixture of vegetable or animal oils,
  - the double bond or the at least one of the double bonds of said lipid derivative being functionalized by a group selected from the epoxy, amine, alcohol and acid groups,
- m corresponding to the number of hydroxyls of the polyol from which X originated is an integer comprised between 2 and 10 and
- n, the number of additional reducing carbohydrates, is less than or equal to m-2.

Thus, according to the invention, the compounds are fatty acid polyester derivatives of biglycosides, triglycosides, tetraglucosides, pentaglucosides, hexaglucosides, heptaglucosides, octaglucosides, nonaglucosides or decaglucosides.

Advantageously, X is a chemical structure bearing hydroxy groups originating from a polyol selected from glycerol, xylitol, phloroglucinol, erythritol, pentaerythritol, dipentaerythritol, arabitol, ribitol, sorbitol, dulcitol, mannitol, volemitol, maltitol, isomaltitol and lactitol, or a diol selected from the diols corresponding to one of the following formulae:

| Name | Formula |
|---|---|
| 1,3-propanediol | HO~~~OH |
| 1,4-butanediol | HO~(~)₂~OH |
| 1,5-pentanediol | HO~(~)₃~OH |
| 1,12-dodecanediol | HO~(~)₁₀~OH |
| diethylene glycol | HO~~O~~OH |
| pentaethylene glycol | HO~~(O~~)₄OH |
| 2-butene-1,4-diol | HO—\\=/—OH |
| 2-butyne-1,4-diol | HO—C≡C—OH |
| 1,4-cyclohexanediol | HO—⬡—OH |
| 2,5-bis(hydroxymethyl) tetrahydrofuran | HO—\\<O>/—OH |
| 1,4-bis(hydroxymethyl) cyclohexane | HO—CH₂—⬡—CH₂—OH |
| Isosorbide | (bicyclic structure) |
| 2,5-bis(hydroxymethyl) furan | HO—CH₂—<furan>—CH₂—OH |
| 1,4-bis(hydroxymethyl) benzene | HO—CH₂—⌬—CH₂—OH |
| Catechol | HO—⌬—OH (ortho) |
| Resorcinol | HO—⌬—OH (meta) |

| Name | Formula |
|---|---|
| Hydroquinone | 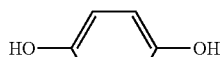 |
| 4,4'-dihydroxybiphenyl |  |
| 2,6-dihydroxynaphthalene | 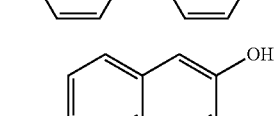 |

In another advantageous embodiment of the invention, the fatty acid polyester derivatives of polyglycosides correspond to formula (Ia)

A-O—X—O—Z  (Ia)

in which
A and Z each represent, independently of each other, a reducing carbohydrate selected from the group of monosaccharides comprising glucose, fructose, galactose and mannose or from the group of the disaccharides comprising lactose and maltose,
said monosaccharides and said disaccharides being bound to —O—X—O— by their anomeric carbon initially bearing the hemiacetal OH,
at least one of the other OH groups of said monosaccharide or said disaccharide being esterified by a lipid derivative bearing at least one double bond optionally originating from a vegetable or animal oil or from a mixture of vegetable or animal oils,
the double bond or the at least one of the double bonds of said lipid derivative being functionalized by a group selected from the epoxy, amine, alcohol and acid groups and
X is the chemical structure bearing hydroxy functions in a compound selected from the group comprising the aliphatic, cycloaliphatic and aromatic polyols, This formula (Ia) is derived from formula (I) considering m=2 therefore n=0.

Thus when X is the chemical structure bearing hydroxy functions originating respectively from glycerol, xylitol, erythritol, propanediol or hydroquinone, then X represents respectively:

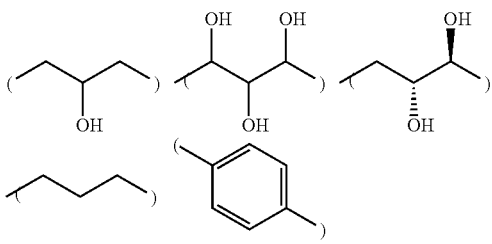

or (— and —) represent the attachment point of O-A and O—Z and/or the other OH functions can also be esterified by mono- or disaccharides such as those mentioned above.

The lipid derivatives are either commercially available or prepared by techniques known to a person skilled in the art. The chains comprise between 4 and 36 carbon atoms ($C_4$-$C_{36}$ chain), advantageously between 12 and 20 carbon atoms ($C_{12}$-$C_{20}$ chain). They can originate from vegetable oils, among which there may be mentioned the vegetable oils of flaxseed, sunflower, rapeseed, hemp, sage, soya, olive, grape seed, Tung wood, bitter melon, cotton, maize, hazelnut, walnut, coconut, avocado, palm, castor-oil plants, safflower, wheat germ, Syrian squash, cashew nuts and peanuts, or animal oils such as for example lard, beef tallow, duck fat, and fish oils (salmon, sardine, anchovy, mackerel, tuna, herring etc.). According to the invention, when these oils are used, it is possible to use the oils alone, or mixtures of oils independently of their origin, vegetable or animal.

In an advantageous embodiment of the invention, in the fatty acid polyester derivatives of polyglycosides according to the invention, the lipid derivative is selected from the mono- or polyunsaturated fatty acids and the mono- or polyunsaturated fatty acid esters. By way of example, the fatty acids and derivatives thereof comprising between 1 and 6 unsaturations, advantageously between 2 and 3 unsaturations, may be mentioned. According to the invention, the fatty acids are selected from arachidonic acid, docosahexaenoic acid, eicosapentaenoic acid, erucic acid, linoleic acid, linolenic acid, eleostearic acid, nervonic acid, oleic acid, palmitoleic acid, ricinoleic acid, vernolic acid. The fatty acid derivatives are in particular selected from the fatty acid esters, such as for example methyl oleate or methyl linoleate, the fatty amides obtained by amidification of fatty acids, and the fatty thioesters originating from the thioesterification of fatty acids, in particular of the fatty acids according to the invention.

In an advantageous embodiment of the invention, in the fatty acid polyester derivatives of polyglycosides, A and Z, identical or different, each represent a glucose unit of formula (II)

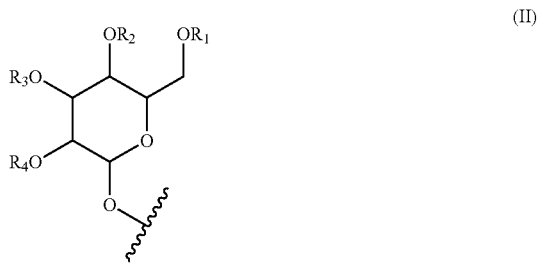

in which
$R_1$, $R_2$, $R_3$ and $R_4$, identical or different, each represent:
either a hydrogen atom,
or a —C(O)($C_4$-$C_{36}$)alkyl group, advantageously a —C(O)($C_{12}$-$C_{20}$)alkyl group, originating from a saturated fatty acid originating from a vegetable or animal oil or from a mixture of vegetable or animal oils,
or a —C(O)($C_4$-$C_{36}$)alkenyl group, advantageously a —C(O)($C_{12}$-$C_{20}$)alkenyl group, originating from an unsaturated fatty acid originating from a vegetable or animal oil or from a mixture of vegetable or animal oils, said group being able to bear, after chemical functionalization of at least one of its double bonds, a functional group selected from the epoxy, amine, alcohol and acid functions, and if several double bonds are functionalized, then the functionality is identical for all the double bonds of said —C(O)($C_4$-$C_{36}$)alkenyl group, and provided that at least one of $R_1$, $R_2$, $R_3$ and $R_4$ is a —C(O)($C_4$-$C_{36}$)alkenyl group functionalized as defined previously.

The invention allows the parallel use of several fatty acids or fatty acid esters. Moreover, a biglucoside X derivative according to the invention could be represented by formula (Ib) below:

In a particularly advantageous embodiment of the invention, X is a residue of 1,3-propanediol or a residue of hydroquinone.

According to the invention, The derivatives can be prepared by any technique known to a person skilled in the art, described in the literature, from products that are commercially available or described in the literature.

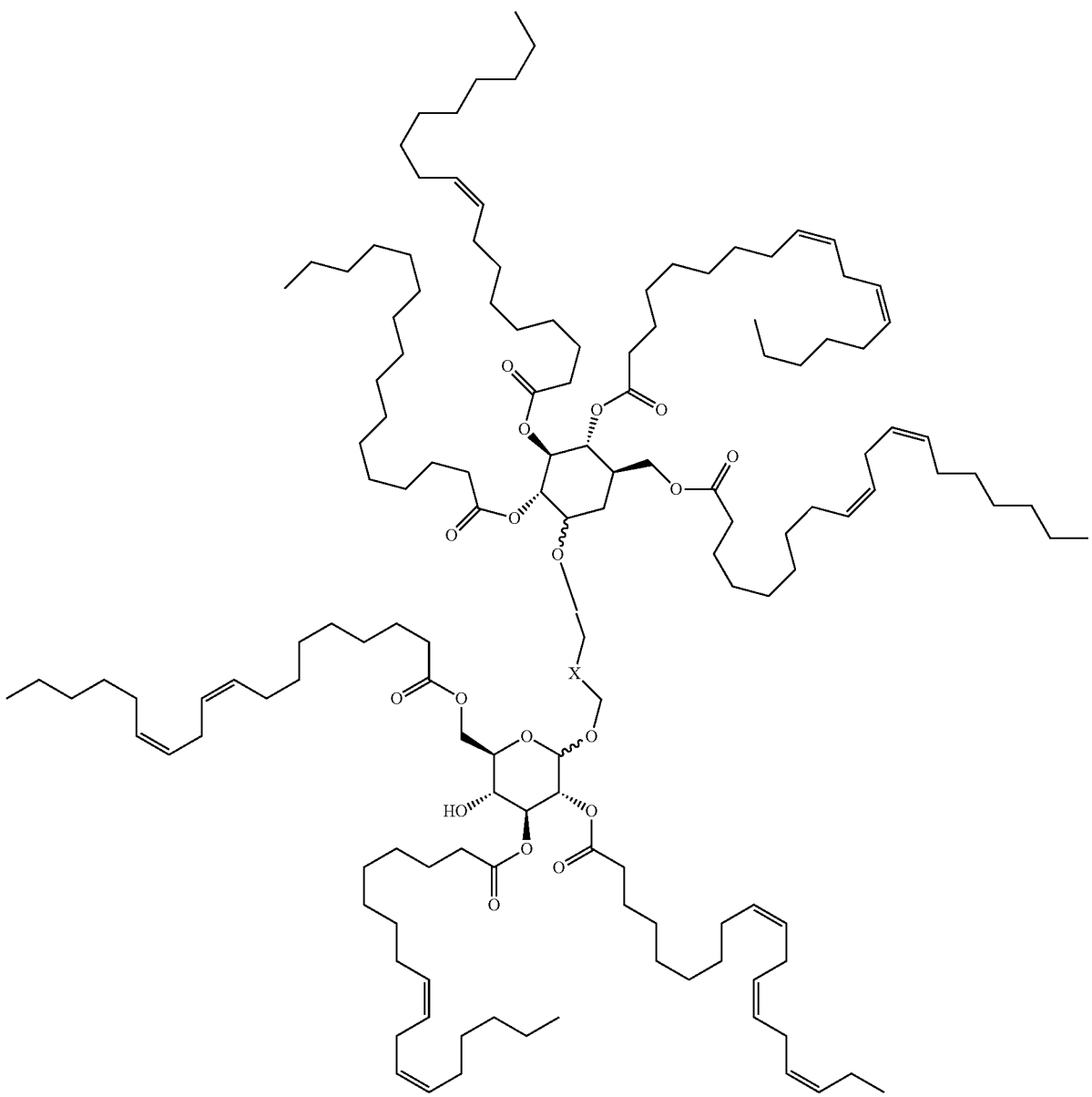

(Ib)

in which X is as defined previously. This formula, presented by way of example, corresponds to a formula (Ia) in which A is a glucose bearing 4 fatty chains derived from methyl stearate (no unsaturation), methyl oleate (one unsaturation), or also methyl linoleate (two unsaturations) respectively, while Z is a glucose bearing 3 fatty chains derived from methyl linoleate (two unsaturations) or methyl linolenate (three unsaturations) respectively.

Thus, they can be obtained for example by a process comprising 3 steps:
- a step of "glycosidation" of the glycosyl donor or a step of glycosylation of the acceptor (the polyol) making it possible to obtain the bare polyglycoside, i.e. without grafting the fatty chains,
- a step of grafting the fatty chains, for example by interesterification in the case of fatty acid ethers reacting with peracetylated glycosyl units and a step of functionalization of the double bonds, for example by epoxidation by the peracid route based on the combined use of acetic acid and hydrogen peroxide in the presence of an ion-exchange resin (Amberlite 120H type).

The step of synthesis of the polyglycosides can be carried out for example by one of the following techniques:
- glycosylation of aglycones of a polyol nature with a glycosyl donor catalyzed by a Lewis acid according to the methodology of Smits, E., et al. (3. Chem. Soc., Perkin Trans. 1, 1996 p. 2873-2877) or that described in international application WO2004/007516, or
- glycosidation involving glycosyl donors such as for example bromides, chlorides, thioimidates or thiocyanates and catalysts such as for example $SnCl_4$, TMSOTf, $FeCl_3$ or $TrClO_4$,
- pre-activation of an aglycone,
- "click chemistry" as described by Neto, V. et al., Tetrahedron, 2010, p. 4633-4646 and Marra, A., et al. J. Org. Chem., 2008, p. 2458-2461,
- Sonogashira-Heck-Cassar (palladium) coupling according to the technique of Dondoni, A., et al. 2002, p. 1850-1854.
- metathesis catalyzed by ruthenium according to the technique of Neto V. et al. (op. cit.) or that of Roy, R. et al. Chem. Commun. (Cambridge), 2000, p. 519-529,
- Ullman (palladium) coupling according to the technique of Bergeron-Brlek, M., et al. J. Org. Chem., 2012, p. 2971-2977,
- Heck (palladium) coupling according to the technique of Giguere, D., et al. Bioorg. Med. Chem., 2008, p. 7811-7823,
- Glaser coupling according to the technique of Siemsen, P., et al. Angew. Chem., Int. Ed., 2000, p. 2632-2657.

The second step can be carried out for example:
- by the interesterification of peracetylated bisglucosides X with lipid derivatives, for example with fatty acid methyl esters (FAME) such as methyl oleate, in the presence of sodium or a sodium salt such as sodium methanolate. These techniques are described in particular by Akoh, C. C. et al. (J. Food Sci., vol. 55, 1990, p. 236-243; J. Food Sci., vol. 52, 1987, p. 1570-1576; J. Am. Oil Chem. Soc., vol. 66, 1989, p. 1581-1587), Mieth, G., et al. (Nahrung, vol. 27, 1983, p. 747-751) and in applications DD156263 and U.S. Pat. No. 4,973, 489 or
- by transesterification between non-protected carbohydrates with FAMEs according to the process described in international application WO9938875.

The third step is the functionalization of the unsaturations borne by the fatty chains, which can be carried out by various approaches illustrated in the figure below and which makes use of techniques known to a person skilled in the art.

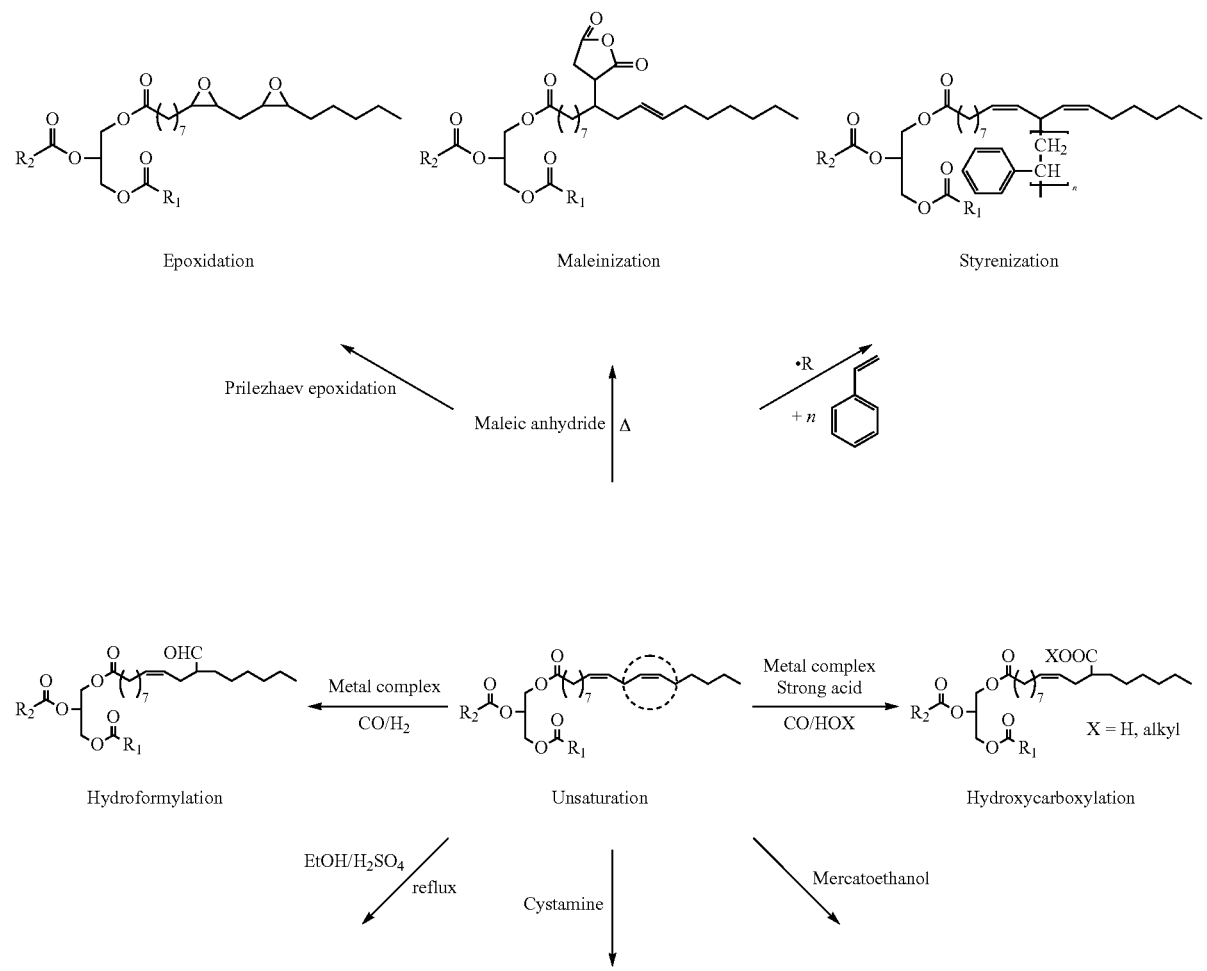

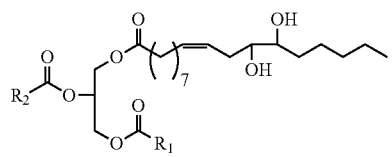 Hydroxylation

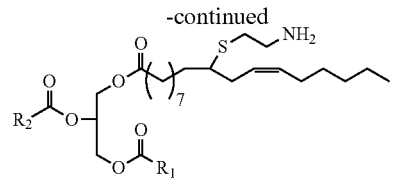 Thiol-ene coupling

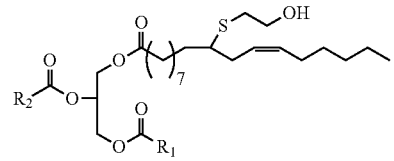 Thiol-ene coupling

When the functionalization of the double bonds consists of an epoxidation, it can be carried out for example by the technique described by Pan, X., et al., Green Chem., 2011, p. 965-975 and in international application WO2011/097484.

When it is a thio-ene coupling (TEC), the functionalization can be carried out by radical addition to the C=C double bonds of mercaptoethanol according to the technique of Desroches, M., et al. Polymer Reviews, 2012. 52(1): p. 38-79 or of cysteamine hydrochloride (CAHC) according to the technique of Stemmelen, M., et al. Journal of Polymer Science Part a—Polymer Chemistry, 2011. 49(11): p. 2434-2444. This reaction can be carried out by thermal route or by photochemical route under UV.

The third step can also consist of:
a styrenization which consists of creating, in a first step, radicals on the allyl carbons by means of the thermal decomposition of a radical initiator such as benzoyl peroxide. The sites thus activated make it possible, by the homopolymerization of styrene, to implant polystyrene grafts onto the fatty acid chains according to the technique of Guner, F. S., et al. Progress in Polymer Science, 2006. 31(7): p. 633-670, a hydroformylation also called "oxo-process" which makes it possible to introduce, via the unsaturations, an aldehyde function onto the lipid chains using a metal complex generally based on cobalt according to the technique of Kandanarachchi, P., et al. Journal of Molecular Catalysis a-Chemical, 2002. 184(1-2): p. 65-71, a hydroxycarboxylation or a Koch reaction which make it possible to introduce carboxylic acid functions onto the double bonds of the lipid segments, according to the technique of Corma, A., et al., Chemical Reviews, 2007. 107(6): p. 2411-2502, a maleinization which makes it possible to graft maleic anhydride units onto the fatty chains according to the technique of Stefanoiu, F., et al. European Journal of Lipid Science and Technology, 2008. 110(5): p. 441-447.

The derivatives according to the invention can be used in order to produce liquid or solid formulations which are novel and form part of the invention. By "formulation" is meant a mixture of at least two reactive compounds. For example, according to this terminology, an epoxy formulation will denote the reaction mixture of at least one epoxy functionalized molecule (=prepolymer) with at least one hardener (polyamine, polyacid, cyclic anhydride etc.)

A subject of the invention is also liquid or solid formulations comprising at least one derivative according to the invention and optionally a cross-linking agent.

When the third step is an epoxidation, then an epoxy prepolymer is obtained that is capable of being included in the composition of thermosetting resins, and at the same time allowing the production of materials by reaction with various cross-linking agents, biosourced or not, such as the diacid anhydrides, compounds bearing primary or secondary amines such as the diamines, polyamines and mixtures thereof, advantageously the diamines, diacids and polyacids, the alcohols, including the phenols, and the polymercaptans.

As examples of diacid anhydrides, there may be mentioned: succinic anhydride, maleic anhydride, dodecenylsuccinic anhydride, phthalic anhydride, hexahydrophthalic anhydride, methylhexahydrophthalic anhydride, methyl-tetrahydrophthalic anhydride, methyl-endo-methylenetetrahydrophthalic anhydride, citric acid anhydride, oxalic acid anhydride, itaconic anhydride and aconitic anhydride.

As examples of amines, of biosourced origin or not, there may be mentioned: the aliphatic diamines such as for example ethylenediamine, hexamethylenediamine, bis(3-aminopropyl)amine, 1,10-decanediamine, 1,4-butanediamine, 1,5-pentanediamine, 1,12-dodecanediamine or 1,18-octadecanediamine, the cycloaliphatic diamines such as isophorone diamine (IPDA), the aromatic diamines such as phenylnediamine in its ortho, meta and para forms, xylylenediamine in its ortho, meta and para forms, 2,5-diaminotoluene, 4,4'-diaminobiphenyl, 4,4'-diaminodiphenylmethane or lysine, the polyamines bearing at least 5 N—H groups, in particular diethylenetriamine, triethylenetetramine, tetraethylenepentamine, poly(oxypropylene) triamine and the polyetheramines, the polyoxyalkyleneamines or the natural polypeptides.

As examples of diacids, there may be mentioned: heptanedioic acid, phthalic acid, isophthalic acid, fumaric acid, maleic acid, terephthalic acid, succinic acid, itaconic acid, aconitic acid, hexahydrophthalic acid, methyl hexahydrophthalic acid, tetrahydrophthalic acid, methyl tetrahydrophthalic acid and pyromellitic acid.

As examples of polymercaptans or polythiols, there may be mentioned: 1,2,5-trimercapto-4-thiapentane, 3,3-dimercaptomethyl-1,5-dimercapto-2,4-dithiapentane, 3-mercapto-methyl-1,5-dimercapto-2,4-dithiapentane, 3-mercaptomethylthio-1,7-dimercapto-2,6-dithiaheptane, 1,2,7-trimercapto-4,6-dithiaheptane, 3,6-dimercaptomethyl-1,9-dimercapto-2,5,8-trithianonane, 1,2,9-trimercapto-4,6,8-trithianonane, 3,7-dimercaptomethyl-1,9-dimercapto-2,5,8-trithianonane, 4,6-dimercaptomethyl-1,9-dimercapto-2,5,8-trithianonane, 3-mercaptomethyl-1,6-dimercapto-2,5-dithiahexane, 3-mercaptomethylthio-1,5-dimercapto-2-thiapentane, 1,1,2,2-tetrakis (mercaptomethylthio)ethane, 1,1,3,3-tetrakis(mercaptomethylthio)propane, 1,4,8,11-tetramercapto-2,6,10-trithiaundecane, 1,4,9,12-tetramercapto-2,6,7,11-tetrathiadodecane, 2,3-dithia-1,4-butanedithiol, and 2,3,5,6-tetrathia-1,7-heptanedithiol, 2,3,5,6,8,9-hexathia-, 10-decanedithiol etc.

A subject of the invention is also biosourced epoxy resins comprising the reaction product of one or more derivatives according to the invention, with at least one cross-linking agent, and optionally in the presence of at least one co-reagent selected from the glycidyl ether derivatives of biosourced polyols such as those described in international application WO2013/124574.

One of the preferential functionalization routes is that based on thiolene chemistry (thiol-ene coupling in the above figure) which consists of being able to react on the unsaturations an R—SH graft where R is a molecular segment allowing the implantation of a novel chemical termination. For example, the use of cysteamine makes it possible to graft onto the lipid chains of short molecular segments terminated by amine groups and, at the same time, to change the building block according to the invention to polyamine. This polyamine can in particular be upgraded as a cross-linking agent for epoxy resins. Thus, it is possible to produce a formulation based entirely on the derivatives according to the invention since the lipid polyester structure can be functionalized in this way. One derivative can be used to produce the epoxy prepolymer when another can be modified by thiolene chemistry in order to synthesize the polyamine-type cross-linking agent. After mixing these two molecules, preferentially in a stoichiometric quantity (iso-proportion of epoxy groups and amine groups), it is possible, by a cross-linking reaction, to produce a material the final performances of which depend on:

- the functionality of the central spacer (diol or polyol),
- the nature thereof (aliphatic, aromatic or cycloaliphatic),
- the actual nature of the selected reducing glycoside units,
- the quantity of unsaturated lipid chains initially grafted onto the glycoside units,
- the number of unsaturations borne by each fatty chain (comprised between 1 and 6),
- the chemical functionalization (amine, carboxylic acid, alcohol etc.) of these same unsaturations for producing the cross-linking agent,
- the degree of epoxidation (case of prepolymer production).

The invention makes it possible to produce alternative solutions to numerous petrochemical formulations whether via the development of prepolymer architectures such as the polyepoxy compounds, or different classes of hardeners (polyamines, polyanhydrides, polyacids etc.). Other classes of polymers are accessible, such as polyurethanes or polyamides, due to the advent of polyol structures. The potential market is that covered by petrosourced polymers, in particular relating to technical applications where numerous products are, or are going to be, rendered obsolete because they are toxic (composite matrices, adhesives, paints, lacquers, electrical insulation etc.). With respect to the epoxy prepolymers alone, the main strength of the invention is the production of rigid structures without epichlorohydrin and without Bisphenol A.

A subject of the invention is therefore the use of these derivatives as prepolymers for the manufacture of polymers selected from the group comprising in particular the polyesters, polyamides, polyurethanes and epoxy resins.

These polymers can be prepared from the derivatives according to the present invention by any technique known to a person skilled in the art, in particular by chemical or physical modification.

The methods of implementation are relatively numerous. If only those conventionally used with thermosets are adopted, processes of the following types may be mentioned: SMC (Sheet Moulding Compound), BMC (Bulk Moulding Composite), preimpregnated, RTM (Resin Transfer Moulding) pultrusion, infusion, thermoforming or also filament winding. These processes require the use of a resin with a well-defined viscosity, which can be modulated according to the invention due to the nature and functionality of the central core, the nature of the reducing glycoside units retained, the quantity of lipid chains grafted onto each glucoside unit as well as the density and the nature of the chemical functionalization of their unsaturation. For example, with identical grafting and functionality, the molecules with an aromatic core will display a significantly higher viscosity than that observed with molecules the central structure of which is aliphatic. The density of the functionalization is another effective parameter for adjusting the initial viscosity of the resin (see Example 1 in the case of epoxy systems). It is thus possible to prepare molecules which will produce fluid systems that are perfectly suitable for direct impregnation processes (infusion, RTM, filament winding etc.) or, conversely, resins with a high viscosity necessary for use thereof, by techniques for SMC, BMC or even preimpregnated substances. Examples 5 and 6 in particular illustrate this concept via the application of the invention to the development of epoxy prepolymers.

A subject of the invention is thus materials obtained by chemical or physical modification of a formulation according to the invention.

BRIEF DESCRIPTION OF THE DRAWINGS

Examples 1 to 6 and FIGS. 1 and 3 which follow, illustrate the invention without however limiting it.

FIG. 5 allows direct comparison of the thermomechanical profile of the cross-linked matrix BGH16E-IPDA with that characteristic of the material obtained from the stoichiometric mixture of epoxidized linseed oil (ELO) hardened with the same cross-linking agent (IPDA). The continuous curves are characteristic of the "storage modulus" G' of each matrix while the dotted curves represent the development of the "loss modulus" G". The glass transition temperature is again assessed at the maximum of the G" curve. Beyond the number of epoxy functions per molecule (16 for BGH16E and 6 for ELO), this figure above all illustrates the influence of the molecular core of the epoxy prepolymer (BGH in the case of the BGH16E and glycerol in the case of the ELO) on the thermomechanical properties of each matrix after cross-linking.

DETAILED DESCRIPTION

Figure 1:
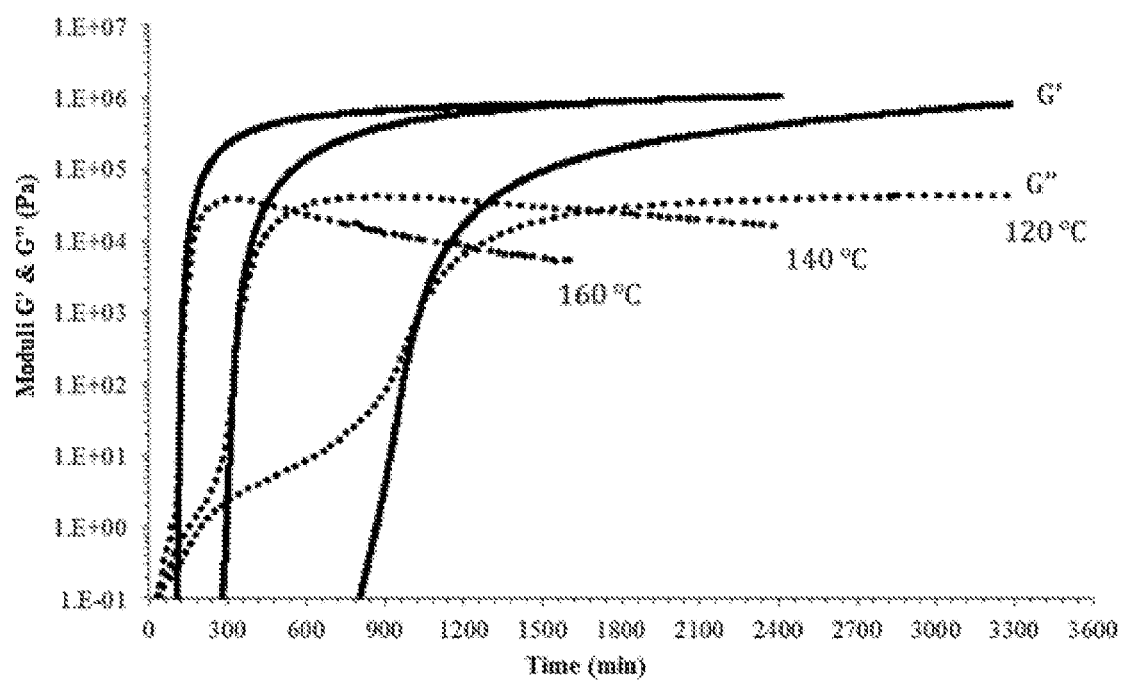
FIG. 1 illustrates the cross-linking kinetics of the BGH8E-IPDA mixture prepared according to Example 4 for different cross-linking temperatures, 120° C., 140° C. and 160° C. The curves represent the kinetic development of the viscoelastic components of said reaction mixture. Component G' (continuous curves) is called the "storage modulus"; it expresses the energy stored, then restored by the material and illustrates its mechanical rigidity. Component G" (dotted curves) denotes the "loss modulus" characteristic of the mechanical energy dissipated due to the molecular movements occurring within the material.

Example 1: General Synthesis of a Fatty Acid Polyester of Biglycosides 1.1. Preparation of Peracetylated Biglucoside X

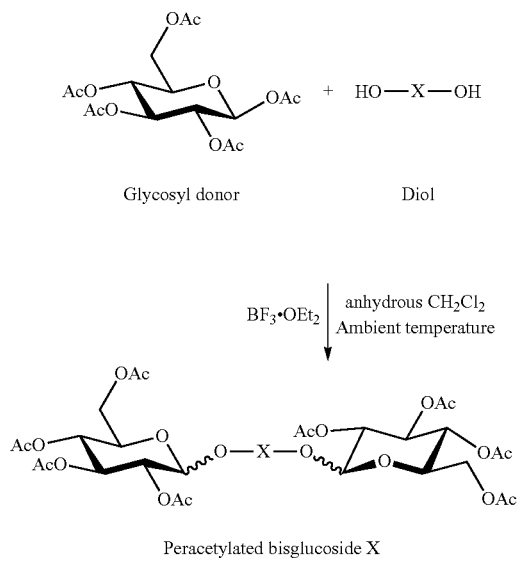

According to the above diagram, β-D-Glucose pentaacetate (β-D-Glc(OAc)$_5$) is used as glycosyl donor. It exists commercially, or can be easily obtained by the action of acetic anhydride on glucose (according to the peracetylation technique known to a person skilled in the art). The diol is represented by the formula HO—X—OH. The glycosyl donor and the diol are solubilized in anhydrous dichloromethane (CH$_2$Cl$_2$). Then boron trifluoride etherate (BF$_3$.OEt$_2$) is added dropwise to the reaction mixture in a glycosyl donor/HO—X—OH/BF$_3$.OEt$_2$ molar ratio of 1:0.5:1. The reaction medium is stirred at ambient temperature for 24 h under an inert atmosphere (nitrogen). The organic phase is purified by liquid-liquid extraction with a saturated aqueous solution of sodium hydrogen carbonate (NaHCO$_3$) then sodium chloride (NaCl). The organic phase is dried with magnesium sulphate (MgSO$_4$) then concentrated by evaporation of the CH$_2$Cl$_2$ under reduced pressure. The biglucosides X (also denoted by the term bisglucosides and abbreviated to BGX) are isolated by column chromatography or by recrystallization depending on the nature of the diol.
The yields of the bisglucosides BGX and any by-products depend on the nucleophile of the diol.

1.2. Interesterification (Ester-Ester Exchange)

The reaction involved in the synthesis of bisglucoside polyesters from fatty acids by interesterification is given in the diagram below, where R represents a lipid chain and R$_1$ a bisglucoside

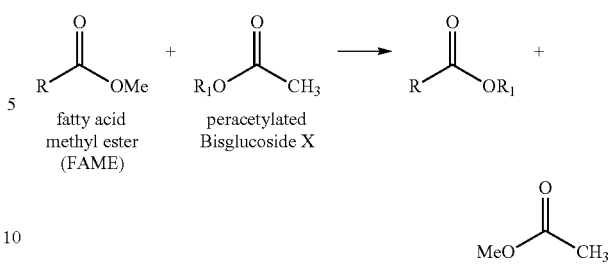

The peracetylated bisglucoside X obtained in step 1.1, the fatty acid methyl ester (FAME) and 2% of Na expressed as the total mass of the mixture are mixed and interesterification is carried out at 110-120° C. for 2-6 h under a reduced pressure comprised between 0 and 667 Pa (0-5 mm Hg) in order to trap the methyl acetate formed. The acetate group: FAME molar ratio is 1:1.
On completion of the reaction, the reaction mixture is diluted while hot with hexane then neutralized with acetic acid. The organic phase is purified by liquid-liquid extraction with methanol. The Bisglucoside Polyesters with a high DS of 5-8 are isolated after evaporation of the hexane under reduced pressure. The average degree of substitution of the mixture is determined by $^1$H NMR and MALDI.

1.3. Functionalization of the Double Bonds 1.3.1. Epoxidation

The fatty acid bisglucoside polyesters (BGP) having "n" moles of double bonds obtained according to step 1.2, acetic acid and Amberlite 120H resin (20% by mass of the mass of BGP) are introduced into a reactor with mechanical stirring. The acetic acid/H$_2$O$_2$/double bonds molar ratio is 0.5:2:1. The reaction mixture is mixed under an inert atmosphere and heated to approximately 60-70° C. in order to reduce the viscosity of the BGP and thus obtain a homogeneous mixture. Hydrogen peroxide (H$_2$O$_2$; 50% by mass in aqueous solution) is added dropwise. After addition, the reaction mixture is mixed for from 30 min to 4 h depending on the sought degree of epoxidation. On completion of the reaction, the reaction mixture is diluted with diethyl ether, then the resin is filtered. The mixture is purified by liquid-liquid extraction with H$_2$O, then with a saturated aqueous solution of NaHCO$_3$ then NaCl. The organic phase is dried with MgSO$_4$ then evaporated under reduced pressure in order to recover the epoxidized fatty acid bisglucoside polyesters (BGPE). The isolated yields are all greater than 95%.

1.3.2. Functionalization by Thiol-Ene Chemistry

Thermal Route

This method requires the use of an initiator (2,2'-azobisisobutyronitrile or AIBN) at a level of 0.02 eq for 3 eq. of cysteamine hydrochloride (3 eq). The latter dosed so that the [CAHC]/[C═C] molar ratio is equal to 3. The unsaturated fatty acid BisGlucoside Polyesters prepared according to the protocol of step 1.3.2, AIBN and CAHC are solubilized in a 1,4-dioxane-ethanol mixture (70-30). The reaction mixture is heated at 80° C., under stirring, for 24 hours, then filtered using a Büchner funnel. The filtrate is concentrated under vacuum then solubilized in chloroform (100 mL). The solution is washed with a saturated NaCl solution (5×350 mL). The organic phase is dried with MgSO$_4$, then concentrated under vacuum. The yield is of the order of 70%.

Photochemical Route

In an erlenmeyer flask, the unsaturated fatty acid BisGlucoside Polyesters prepared according to the protocol of step 1.3.2, cysteamine hydrochloride (3 eq per double bond present on the lipid chain) and a photoinitiator (2,2-dimethoxy-2-phenylacetophenone, DMPA, dosed at 0.1 eq per [C=C]) are solubilized in a 1,4-dioxane/ethanol mixture (according to the mass ratio 70/30 m/m). The mixture is gently heated to a maximum temperature of 40° C. then left under mechanical stirring until the cysteamine hydrochloride is dissolved. The mixture is then poured into a photoreactor under stirring and UV irradiation for a period of time comprised between 8 and 96 h (variable according to the desired level of functionalization). The temperature is maintained at a value of 20° C. by means of a suitable coolant system. For a low conversion rate, the ethanol can be evaporated and the organic phase is washed with a saturated solution of $Na_2CO_3$. It is then placed at −20° C. for 24 h in order to recrystallize the cysteamine hydrochloride. The latter is then eliminated by filtration using a Buchner funnel (porosity frit 4). The recrystallization-filtration steps are repeated until there is no more cysteamine hydrochloride to recrystallize. The solution is then washed with a saturated $Na_2CO_3$ solution (3×150 mL). The organic phase is dried with $MgSO_4$, then concentrated under vacuum. In order to obtain a high conversion rate, it is necessary to replace the solvents with chloroform. The organic phase is washed and isolated as previously. The conversion rate is of the order of 87 to 90%.

Example 2: Synthesis of BGH8

The BGH8 of formula:

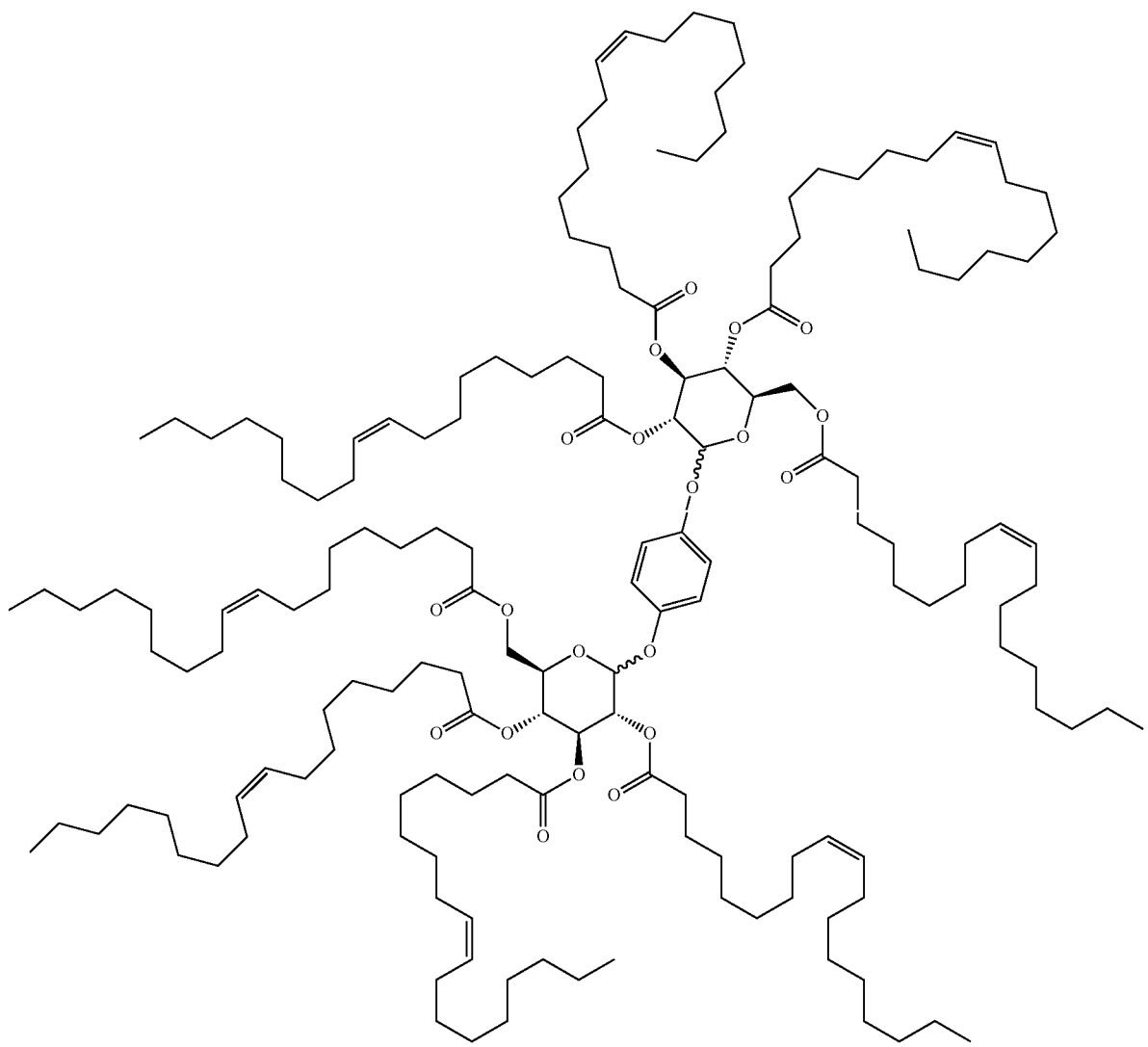 [SMILES: CCCCCCCC/C=C\CCCCCCCC(=O)OC[C@H]1OC(Oc2ccc(OC3O[C@H](COC(=O)CCCCCCC/C=C\CCCCCCCC)[C@@H](OC(=O)CCCCCCC/C=C\CCCCCCCC)[C@H](OC(=O)CCCCCCC/C=C\CCCCCCCC)[C@H]3OC(=O)CCCCCCC/C=C\CCCCCCCC)cc2)[C@H](OC(=O)CCCCCCC/C=C\CCCCCCCC)[C@@H](OC(=O)CCCCCCC/C=C\CCCCCCCC)[C@@H]1OC(=O)CCCCCCC/C=C\CCCCCCCC]

was synthesized according to the general process of Example 1 (steps 1.1 and 1.2) from glucose, hydroquinone and methyl oleate.

Example 3: Synthesis of BGH8E

This compound BGH8E of formula:

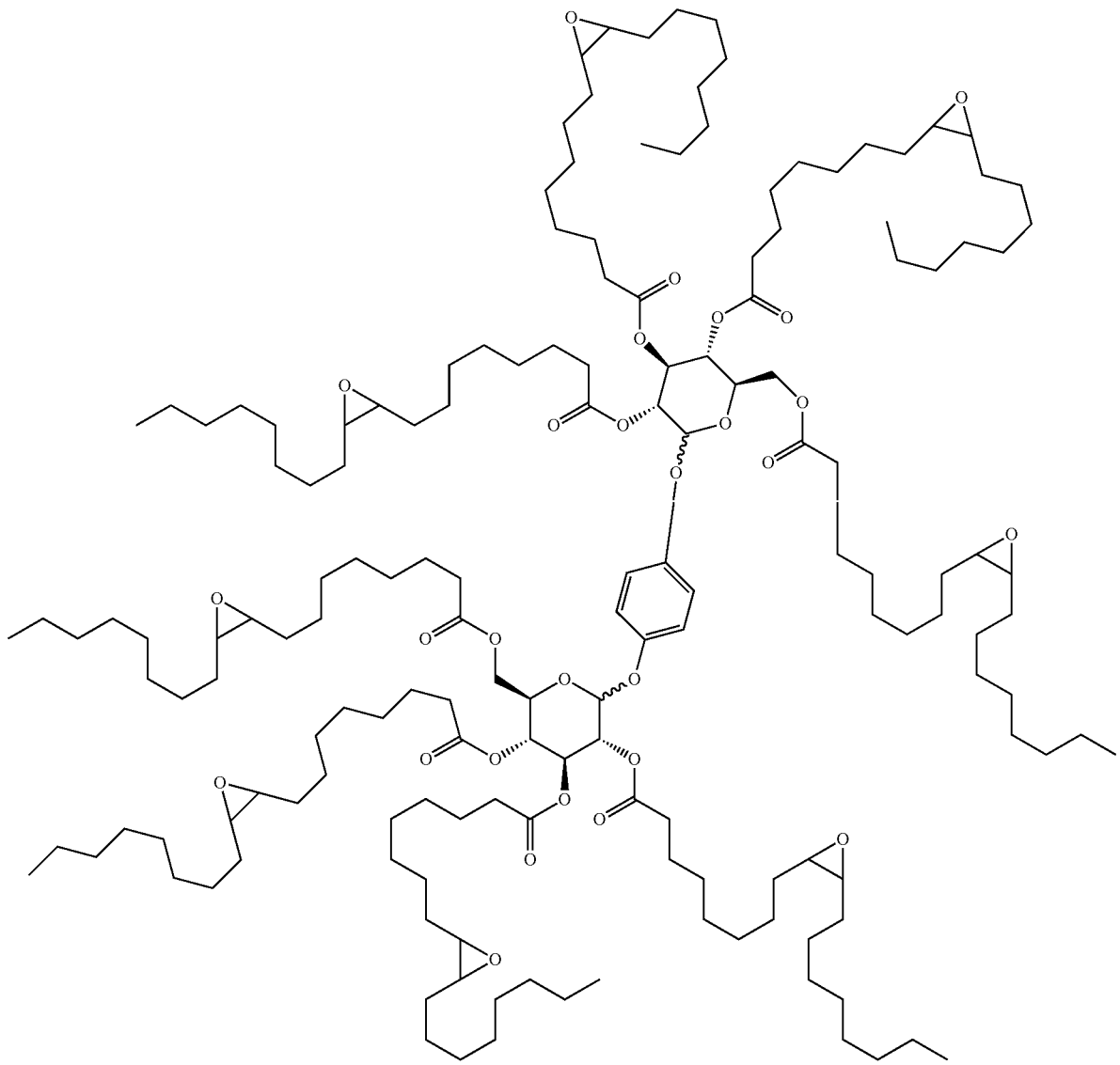 [SMILES: CCCCCCCCC1OC1CCCCCCCC(=O)OC[C@H]1OC(Oc2ccc(OC3O[C@H](COC(=O)CCCCCCCC4OC4CCCCCCCC)[C@@H](OC(=O)CCCCCCCC4OC4CCCCCCCC)[C@H](OC(=O)CCCCCCCC4OC4CCCCCCCC)[C@H]3OC(=O)CCCCCCCC3OC3CCCCCCCC)cc2)[C@H](OC(=O)CCCCCCCC2OC2CCCCCCCC)[C@@H](OC(=O)CCCCCCCC2OC2CCCCCCCC)[C@@H]1OC(=O)CCCCCCCC1OC1CCCCCCCC]

is prepared by epoxidation of the BGH8 of Example 2 according to the protocol described in Example 1.3.1.

Example 4: Epoxy Resin Prepared from BGH8E and Hardener IPDA (BGHSE-IPDA)

4.1. Preparation of the Resin

In this example, the resin is formed by the reaction mixture of the epoxy prepolymer BGH8E with a cycloaliphatic diamine, isophorone diamine (IPDA). The dosing of the prepolymer and the hardener is carried out in order to guarantee complete consumption of the reactive species. The latter requires that the total number of the amine N—H groups is equal to the total number of epoxy groups present in the medium. The BGH8E bears 8 epoxy functions per molecule while the diamine IPDA comprises 4 NH functions per molecule; the associated molar dosage is 1:2. This means that for 100 parts of BGH8E derived from biomass there are 12.7 associated parts of diamine IPDA derived from petrochemicals. The proportion of fossil carbon is therefore low. Concerning the actual mixing phase, the epoxy prepolymer BGH8E is heated to a temperature of 50° C. beforehand, in order to have a low viscosity. The diamine IPDA is liquid as from ambient temperature, but it is heated to the same temperature in order to allow it to be more easily incorporated and mixed with the prepolymer.

The diamine is poured into the prepolymer. Mechanical stirring is carried out for 5 minutes while the temperature of the BGH8-IPDA mixture is kept constant and equal to 50° C.

The reaction mixture is then poured into a suitable mould before carrying out cross-linking at a temperature comprised within the reaction range, the limits of the latter being previously determined by calorimetric analysis.

4.2. Results of BGH8E-IPDA

The cross-linking kinetics is studied by means of isothermal rheological analyses on the reaction mixture. The results obtained at three specific temperatures on fresh mixtures are shown in FIG. 1.

It is thus possible to carefully define the minimum cross-linking times associated with each curing temperature. The material BGH8E-IPDA has thus been produced under optimized time and temperature conditions.

Thus, after complete cross-linking with an amine hardener, BGH8E, which has 8 epoxy groups, makes it possible to obtain a material the performances of which are equivalent to those observed with an equivalent hardener with epoxidized SEFOSE11 (SEFOSE11E) of formula

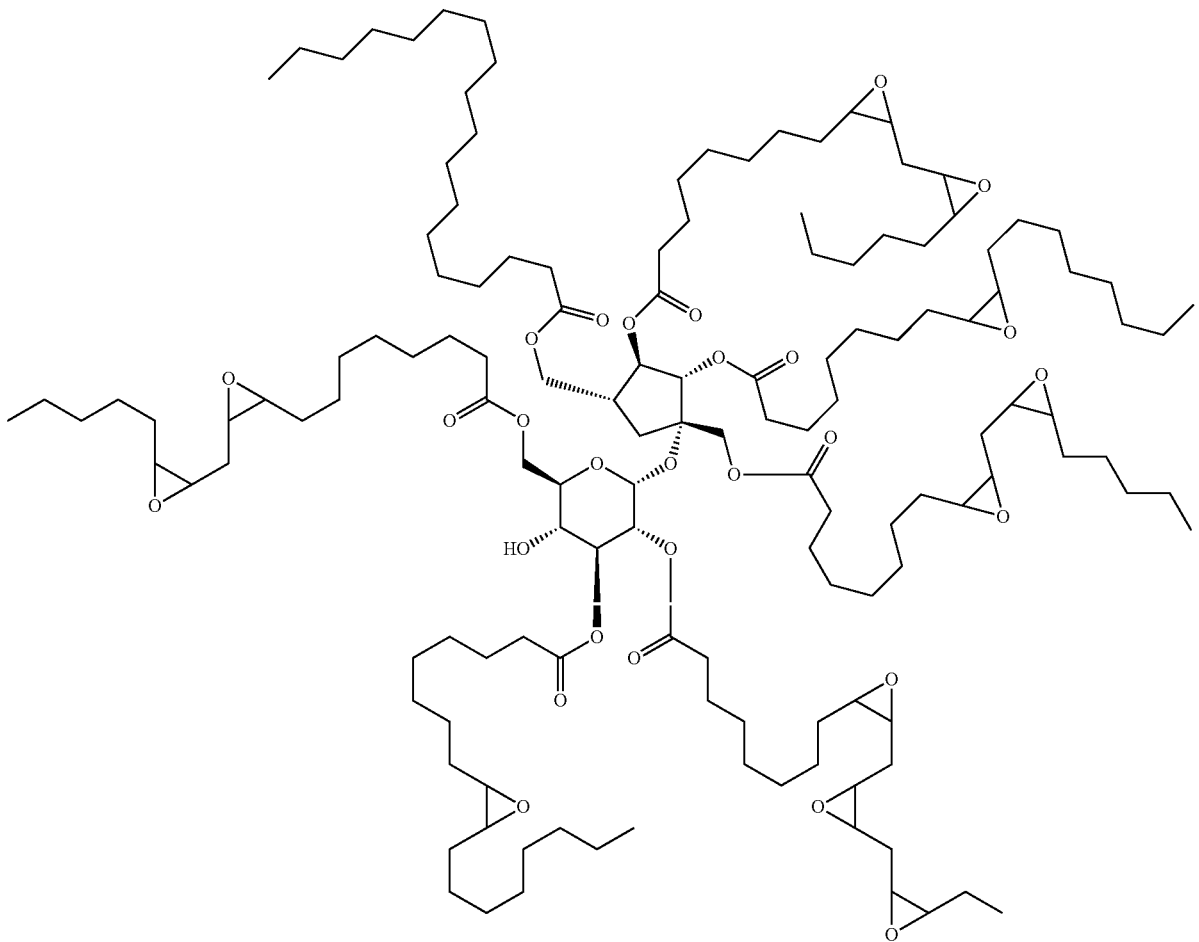 [SMILES: CCCCCCCCCCCCCCCCCC(=O)OC[C@H]1C[C@@](COC(=O)CCCCCCCC2OC2CC2OC2CCCCC)(O[C@H]2O[C@H](COC(=O)CCCCCCCC3OC3CC3OC3CCCCC)[C@@H](O)[C@H](OC(=O)CCCCCCCC3OC3CCCCCCCC)[C@H]2OC(=O)CCCCCCCC2OC2CC2OC2CC2OC2CC)[C@@H](OC(=O)CCCCCCCC2OC2CCCCCCCC)[C@@H]1OC(=O)CCCCCCCC1OC1CC1OC1CCCCC]

described in international application WO 2011/097484 and comprising 11 epoxy groups. In effect, the material BGH8E-IPDA displays a Tg of 18° C. as opposed to 22° C. for the material SEFOSE11E-IPDA.

Example 5: Epoxy Resin Prepared from BGH8E and Hardener MHHPA (BGH8E-MHHPA)

5.1. Preparation of the Resin

In this novel example, the resin is prepared from the mixture of epoxy prepolymer BGH8E and a cross-linking agent of the anhydride type (methylhexahydrophthalic anhydride denoted by the acronym MHHPA). The dosing of the prepolymer and the hardener is carried out according to a ratio of the number of anhydride groups to the number of epoxy groups equal to 0.8 in order to avoid the residual presence of carboxylic acid functions detrimental to the physico-chemical properties of the material. At the molar level, this means dosing 6.4 moles of anhydride functions for one mole of BGH8E. In terms of mass proportions, for 100 parts of BGH8E there are associated 40.1 parts of anhydride MHHPA. 0.4 part of catalyst of the 2-methylimidazole type is added to the reaction mixture.

As regards the actual mixing phase, the epoxy prepolymer BGH8E is heated to a temperature of 50° C. beforehand, in order to have a low viscosity. Although liquid as from ambient temperature, the liquid anhydride is heated to the same temperature in order to allow it to be better incorporated and to facilitate its mixing with the prepolymer.

The anhydride is thus added to the prepolymer, then mechanical stirring is carried out for 5 minutes at a constant temperature equal to 50° C. The catalyst is finally added and the mixture is mechanically stirred for one more minute.

After determining the optimum cross-linking conditions according to the same protocol as that presented in Example 4, the reaction medium is placed in a thermal chamber in order to polymerize.

5.2. Results of BGH8E-MHPPA

The material based on BGH8E displays thermomechanical characteristics far superior to those recorded with the formulation based on the mixture of the SEFOSE11E and the same hardener.

Figure 2:
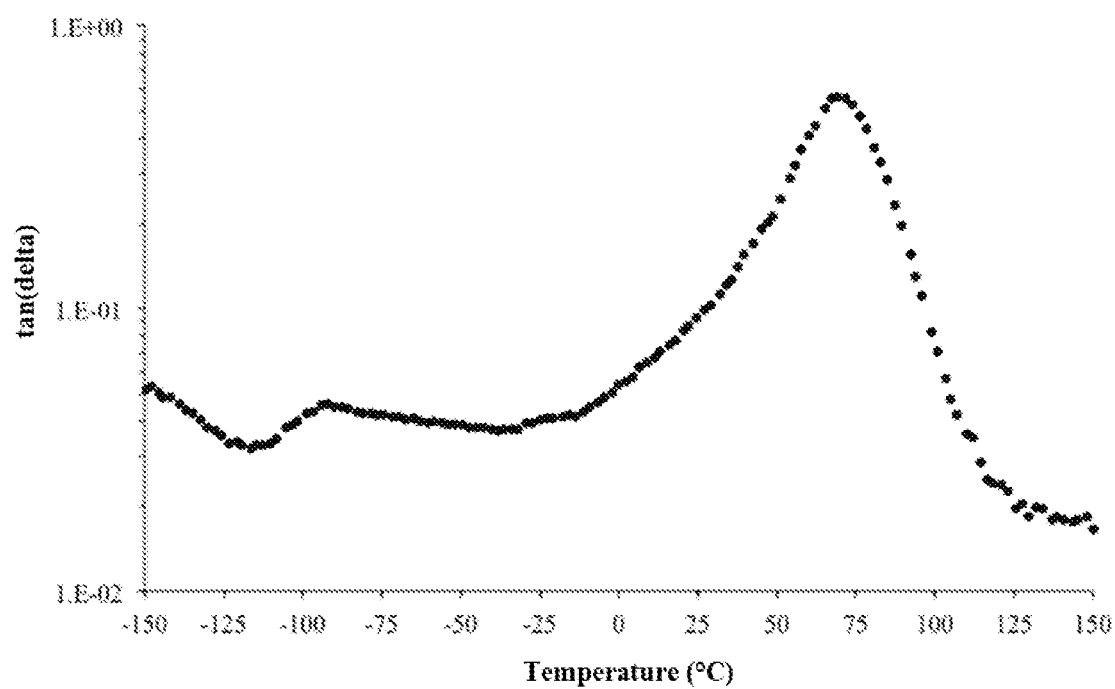
FIG. 2 illustrates the thermomechanical profile of the material BGH8E-MHPPA obtained according to Example 5 after cross-linking at 140° C. for 3 hours. The curve, called tan(delta), is the G"/G' ratio measured at different temperatures.

FIG. 2 demonstrates that after cross-linking at 140° C. for 3 hours, the mechanical relaxation peak of the material is of the order of 70° C. while the SEFOSE11E comprising 11 epoxy functions, after cross-linking with MHHPA, has a temperature of 48.4° C. as reported in Pan et al., Biomacromolecules, 2011. 12(6): p. 2416-2428.

The aromatic central core imparting rigidity to the chemical backbone contributes to the higher glass transition temperature. This result underlines the importance of the adjustment of the central structure since the molecule in question produces better results despite a reduced number of epoxy functions. Conversely, the use of an aliphatic central diol makes it possible to produce a very flexible material.

Example 6: Epoxy Resin Prepared from BGH16E and Hardener MHHPA (BGH16E-MHHPA)

6.1. Preparation of the Resin
6.1.1. Preparation of BGH16E

As stated previously, the invention allows the use of a wide range of fatty acid esters. Thus, by using methyl linoleate instead of methyl oleate, it is possible to produce an epoxidized bisglucoside comprising two epoxy functions per fatty chain, i.e. a total number of 16 epoxy functions per molecule. The general process of Example 1 (steps 1.1 and 1.2) is used, starting from glucose, hydroquinone and methyl linoleate.

6.1.2. Preparation of the Resin

It is prepared according to the procedure of Example 5 from BGH16E and MHPPA. The dosing of the prepolymer and the hardener is carried out according to a ratio of the number of anhydride groups to the number of epoxy groups equal to 0.8 in order to avoid the residual presence of carboxylic acid functions detrimental to the physico-chemical properties of the material. At the molar level, this means dosing 12.8 moles of anhydride functions for one mole of BGH16E. In terms of mass proportions, for 100 parts of BGH16E there are associated 72.3 parts of anhydride MHHPA. 0.7 part of catalyst of the 2-methyl-imidazole type is added to the reaction mixture.

6.2. Results of BGH16E-MHPPA

Figure 3:
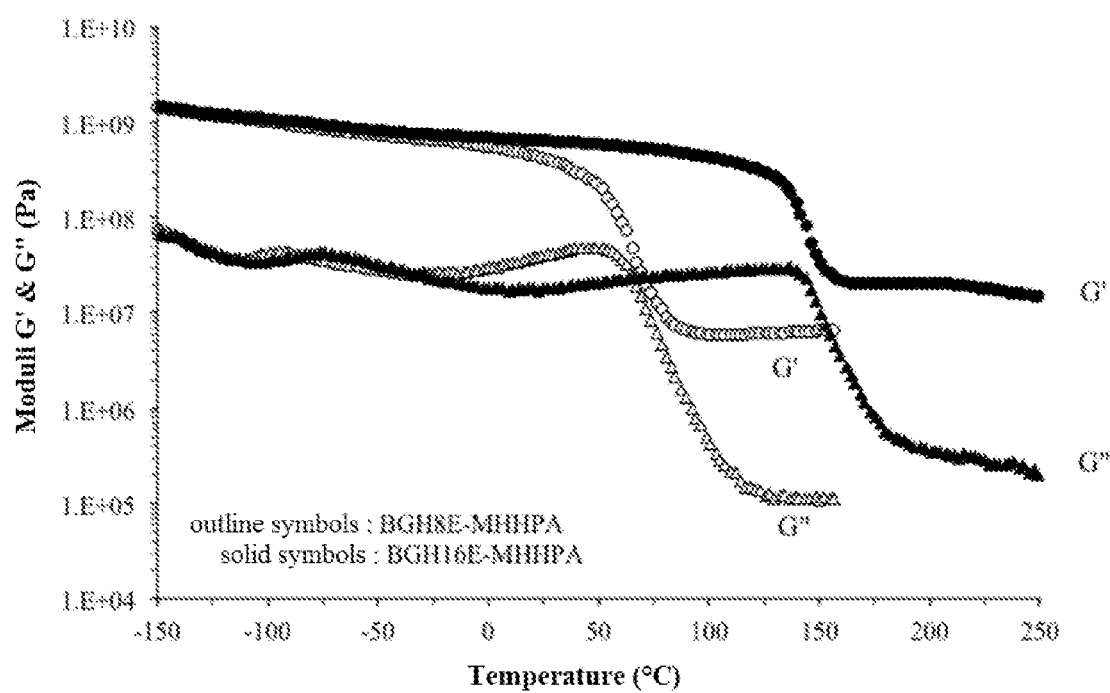
FIG. 3 is a comparison of the thermomechanical responses of the materials BGH8E-MHHPA and BGH16E-MHHPA obtained according to Examples 5 and 6 respectively. The outline symbols denote the response of BGH8E-MHHPA and the solid symbols denote the response of BGH16E-MHHPA. The changes in component G' are represented by the circular symbols (○,●) while those of component G" are represented by the triangular symbols (∆,▲).

This versatility of synthesis is interesting because, if the other items for adjustment of the properties are kept unchanged (i.e. an aromatic core derived from hydroquinone and glucose units, an MHHPA hardener), the final performance level is even higher than with the material BGH8E-MHHPA as illustrated in FIG. 3. The mechanical relaxation peak associated with the glass transition of the material, taken at the maximum of the curve of the loss modulus G", thus increases from 49° C. for BGH8E-MHHPA to 137° C. for BGH16E-MHHPA.

Example 7: Epoxy Resin Prepared from BGH16E and Hardener IPDA (BGH8E-IPDA)

7.1. Preparation of the Resin

BGH16E is prepared according to the procedure of Example 6. It is mixed with the hardener IPDA according to the protocol already detailed in Example 4 with the BGH8E-IPDA combination. The dosing of the prepolymer and the hardener is carried out in order to guarantee complete consumption of the reactive species. The latter requires that the total number of the amine N—H groups is is equal to the total number of epoxy groups present in the medium. As BGH16E bears 16 epoxy functions per molecule while the diamine IPDA comprises 4 NH functions per molecule, the associated molar dosage is 1:4. This means that for 100 parts of biosourced BGH16E there are associated 24.4 parts of diamine IPDA derived from petrochemicals.

7.2. Results of BGH16E-IPDA

Figure 4:
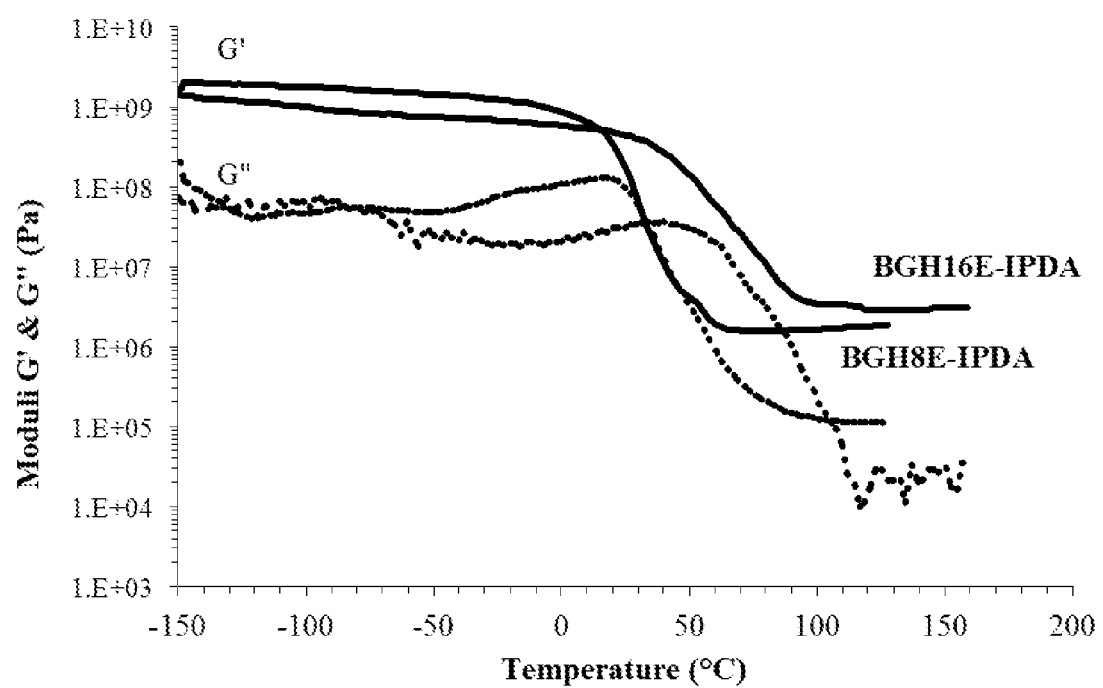
FIG. 4 shows the thermomechanical profiles of the materials obtained by respective cross-linking of the reactive formulations BGH8E-IPDA and GH16E-IPDA. The continuous curves are characteristic of the "storage modulus" G' of each matrix while the dotted curves represent the change in the "loss modulus" G" of these same materials. The glass transition temperature can be assessed by taking the main relaxation temperature, i.e. at the maximum of the G" curve. This series makes it possible to analyze the effect caused by the nature of the lipid chain and indirectly by the number of epoxy functions "x" per molecular unit of BGHxE on the final performances of the matrices using IPDA as hardener.

These are given in FIGS. 4 and 5.

FIG. 4 makes it possible to assess the thermomechanical performances of the cross-linked material starting from the reactive formulation BGH16E-IPDA. The mechanical relaxation peak associated with the glass transition of the material, taken at the maximum of the curve of the loss modulus G", provides a good assessment of the glass transition temperature of this material. It is of the order of 42° C. for BGH16E-IPDA as opposed to 18° C. for the BGH8E-IPDA described previously in Example 4. The effect provided directly by the linoleic chains (in the case of BGH16) instead of oleic chains (in the case of BGH8) can thus be seen. A higher degree of unsaturation (BGH16E relative to BGH8E) allows a higher rate of epoxidation and at the same time a more compact macromolecular mesh, guaranteeing superior thermomechanical performances. On the other hand, if the cross-linked substrate needs to display a greater mechanical flexibility the material BGH8E will be more useful than BGH16E.

FIG. 5 allows direct comparison of the BGH16E-IPDA matrix with that originating from epoxidized linseed oil (ELO) comprising 6 epoxy functions as described in international application WO2012136940. The dosing of the ELO with IPDA is carried out according to a molar ratio of 1:1.5 and it is completely cross-linked at 140° C. over 24 h. The superiority of performances of the material BGH16E-IPDA (Tg=42° C. is undeniable in comparison with those of ELO-IPDA (Tg=11° C.). The superior properties of BGH16E-IPDA are brought about by the higher number of epoxy functions and above all by the presence of the central biglucoside core, the molecular rigidity of which is higher than that of the glycerol core of the ELO.

The invention claimed is:

1. Fatty acid polyester derivatives of polyglycosides produced by a method comprising:
    (a) reacting a polyol comprising between 2 and 10 hydroxyl functional groups with the anomeric carbon of a previously peracetylated reducing carbohydrate selected from the group consisting of monosaccharides, disaccharides, and any mixture thereof, and thereby producing a polyester comprising one or more of ester groups;
    (b) reacting the ester groups of the polyester of step (a) with an ester group of a lipid derivative bearing one or more double bonds, the lipid derivative optionally originating from a vegetable or animal oil or from a mixture of vegetable or animal oils, and
    (c) functionalizing the one or more double bonds with a functional group selected from the epoxide, amine, alcohol and acid groups.

2. The fatty acid polyester derivatives of polyglycosides according to claim 1, characterized in that they correspond to formula (I)

in which
    A and Z each represent, independently of each other, a reducing carbohydrate selected from the group of monosaccharides comprising glucose, fructose, galactose and mannose or from the group of disaccharides comprising lactose and maltose, said monosaccharides and said disaccharides being bound to —O—X—O— by their anomeric carbon initially bearing the hemiacetal OH, at least one of the other OH groups of said monosaccharide or said disaccharide being esterified by a lipid derivative bearing at least one double bond optionally originating from a vegetable or animal oil or from a mixture of vegetable or animal oils, the double bond or the at least one of the double bonds of said lipid derivative being functionalized by a group selected from the epoxy, amine, alcohol and acid groups, X represents a chemical structure bearing hydroxy functions in a compound selected from the group comprising the aliphatic (non-cyclic chains), cycloaliphatic and aromatic polyols, $R_i$ represents either a substituent, or several substituents denoted $R_a$ to $R_h$, said substituents $R_a$ to $R_h$, identical or different, being reducing carbohydrates selected from the group of monosaccharides comprising glucose, fructose, galactose and mannose or from the group of disaccharides comprising lactose and maltose, said monosaccharides and said disaccharides being bound to —O—X—O— by their anomeric carbon initially bearing the hemiacetal OH, at least one of the other OH groups of said monosaccharide or said disaccharide being esterified by a lipid derivative bearing at least one double bond optionally originating from a vegetable or animal oil or from a mixture of vegetable or animal oils, the double bond or the at least one of the double bonds of said lipid derivative being functionalized by a group selected from the epoxy, amine, alcohol and acid groups, m corresponding to the number of hydroxyls of the polyol from which X originated is an integer comprised between 2 and 10; and n, the number of additional reducing carbohydrates is less than or equal to m-2.

3. The derivatives according to claim 1, characterized in that X is a chemical structure bearing hydroxy groups of a polyol selected from glycerol, xylitol, phloroglucinol, erythritol, pentaerythritol, dipentaerythritol, arabitol, ribitol, sorbitol, dulcitol, mannitol, volemitol, maltitol, isomaltitol and lactitol, or a diol selected from the following diols: 1,3-propanediol, 1,4-butanediol, 1,5-pentanediol, 1,12-dodecanediol, pentaethylene glycol, 2-butene-1,4-diol, 2-butyne-1,4-diol, 1,4-cyclohexanediol, 2,5-bis(hydroxymethyl)tetrahydrofuran, 1,4-bis(hydroxymethyl)cyclohexane, isosorbide, 2,5-bis(hydroxymethyl)furan 1,4-bis(hydroxymethyl)benzene, catechol, resorcinol, hydroquinone, 4,4'-dihydroxybiphenyl and 2,6-dihydroxynaphthalene.

4. The fatty acid polyester derivatives of polyglycosides according to claim 1, characterized in that they correspond to formula (Ia)

A-O—X—O—Z (Ia)

in which

A and Z each represent, independently of each other, a reducing carbohydrate selected from the group of monosaccharides comprising glucose, fructose, galactose and mannose or from the group of disaccharides comprising lactose and maltose, said monosaccharides and said disaccharides being bound to —O—X—O— by the anomeric carbon initially bearing the hemiacetal OH, at least one of the other OH groups of said monosaccharide or said disaccharide being esterified by a lipid derivative bearing at least one double bond optionally originating from a vegetable or animal oil or from a mixture of vegetable or animal oils, the double bond or the at least one of the double bonds of said lipid derivative being functionalized by a group selected from the epoxy, amine, alcohol and acid groups; and X is the chemical structure bearing hydroxy functions in a compound selected from the group comprising the aliphatic, cycloaliphatic and aromatic polyols.

5. The derivatives according to claim 1, characterized in that the lipid derivative is selected from the mono- or polyunsaturated fatty acids and the mono- or polyunsaturated fatty acid esters.

6. The derivatives according to claim 1, characterized in that A and Z, identical or different, each represent a glucose unit of formula (II)

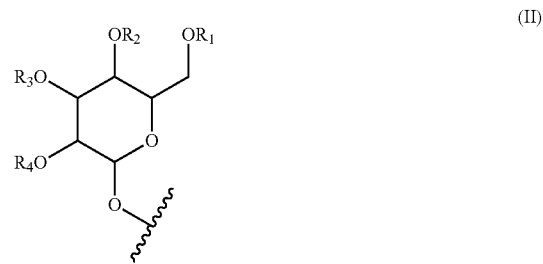

(II)

in which $R_1$, $R_2$, $R_3$ and $R_4$, identical or different, each represent:
either a hydrogen atom, or a $C(O)(C_4-C_{36})$alkyl group, advantageously a $C(O)(C_{12}-C_{20})$alkyl group, originating from a saturated fatty acid originating from a vegetable or animal oil or from a mixture of vegetable or animal oils, or a —$C(O)(C_4-C_{36})$alkenyl group, advantageously a —$C(O)(C_{12}-C_{20})$alkenyl group, originating from an unsaturated fatty acid originating from a vegetable or animal oil or from a mixture of vegetable or animal oils, said group being able to bear, after chemical functionalization of at least one of its double bonds, a functional group selected from the epoxy, amine, alcohol and acid functions, and if several double bonds are functionalized, then the functionality is identical for all the double bonds of said —$C(O)(C_4-C_{36})$alkenyl group; and provided that at least one of $R_1$, $R_2$, $R_3$ and $R_4$ is a —$C(O)(C_4-C_{36})$alkenyl group functionalized as defined previously.

7. The derivatives according to claim 1, characterized in that X is a residue of 1,3-propanediol or a residue of hydroquinone.

8. A liquid or solid formulation comprising: at least one derivative according to claim 1 and optionally a cross-linking agent.

9. Biosourced epoxy resins comprising: the reaction product of one or more derivatives according to claim 1, with at least one cross-linking agent and optionally in the presence of at least one co-reagent selected from the glycidyl ether derivatives of biosourced epoxidized polyols.

10. A material obtained by chemical or physical modification of a formulation according to claim 8.

11. A matrix composite, adhesive, paint, lacquer or electrical insulation comprising the material of claim 10.

12. A fatty acid polyester derivative made by the process comprising:

provided a polyol comprising between 2 and 10 hydroxyl functional groups;

providing a peracetylated reducing carbohydrate selected from the group of monosaccharides consisting of glucose, fructose, galactose and mannose, from the group of disaccharides consisting of lactose and maltose, or any mixture thereof;

reacting said polyol with the anomeric carbon of said peracetylated reducing carbohydrate to form a polyester comprising one or more of ester group reacting according an interesterification pathway said polyester comprising one or more of ester groups with a lipid derivative of a mono or polyunsaturated fatty acid or mono or polyunsaturated fatty acid ester selected from the group consisting of arachidonic acid, docosahexaenoic acid, eicosapentaenoic acid, erucid acid, linoleic acid, linolenic acid, ricinoleic acid, vernolic acid, oleic acid, palmitoleic acid, ricinoleic acid, vernolic acid or methyl esters, amides and thioesters of said fatty acids; and performing the chemical functionalization of double bonds of said interesterified polyester with a functionalization agent selected from the group consisting of either a mixture of acetic acid and hydrogen peroxide or cysteamine hydrochloride and forming the fatty acid polyester derivative.

* * * * *